(12) United States Patent
Watson et al.

(10) Patent No.: US 10,939,621 B2
(45) Date of Patent: Mar. 9, 2021

(54) METHOD AND APPARATUSES FOR COLD PLASMA IN AGRICULTURE

(71) Applicant: Plasmology4, Inc., Scottsdale, AZ (US)

(72) Inventors: Gregory A. Watson, Lake Mary, FL (US); Emilia Kulaga, Scottsdale, AZ (US)

(73) Assignee: Plasmology4, Inc., Scottsdale, AZ (US)

( * ) Notice: Subject to any disclaimer, the term of this patent is extended or adjusted under 35 U.S.C. 154(b) by 154 days.

(21) Appl. No.: 16/191,298

(22) Filed: Nov. 14, 2018

(65) Prior Publication Data

US 2019/0313582 A1    Oct. 17, 2019

Related U.S. Application Data

(60) Provisional application No. 62/585,957, filed on Nov. 14, 2017.

(51) Int. Cl.
| | |
|---|---|
| *A01G 7/00* | (2006.01) |
| *A01C 23/02* | (2006.01) |
| *A01C 23/04* | (2006.01) |
| *A01M 13/00* | (2006.01) |
| *A01C 21/00* | (2006.01) |
| *A61L 2/14* | (2006.01) |
| *A01M 7/00* | (2006.01) |

(52) U.S. Cl.
CPC ............. *A01G 7/00* (2013.01); *A01C 21/00* (2013.01); *A01C 23/023* (2013.01); *A01C 23/047* (2013.01); *A01M 7/0032* (2013.01); *A01M 13/00* (2013.01); *A61L 2/14* (2013.01); *A61L 2202/11* (2013.01)

(58) Field of Classification Search
CPC ..... A01C 23/023; A01C 23/047; A01C 21/00; A01M 7/0032; A01M 13/00; A01G 7/04; A01G 7/00
See application file for complete search history.

(56) References Cited

U.S. PATENT DOCUMENTS

| | | | |
|---|---|---|---|
| 2015/0101082 A1* | 4/2015 | Bormashenko | A01C 1/00 800/298 |
| 2016/0097134 A1* | 4/2016 | Azad | C25B 3/105 530/300 |
| 2018/0327283 A1* | 11/2018 | Pemen | B01J 19/088 |
| 2019/0322550 A1* | 10/2019 | Weltmann | H01J 37/3255 |
| 2020/0071199 A1* | 3/2020 | Lewis, III | H05H 1/48 |

\* cited by examiner

*Primary Examiner* — Monica L Barlow
*Assistant Examiner* — Aaron M Rodziwicz
(74) *Attorney, Agent, or Firm* — Ballard Spahr LLP

(57) ABSTRACT

Methods and systems for generating a plasma-activated liquid or gas, and applying the plasma-activated liquid for agricultural use. A system embodiment includes a hand-held device that can be pointed and directed at different target areas of a plant. A method embodiment includes generating a plasma discharge in a gas environment or a liquid environment, and applying the gas/liquid to a plant.

20 Claims, 4 Drawing Sheets

METHOD AND APPARATUSES FOR COLD PLASMA IN AGRICULTURE

CROSS-REFERENCE TO RELATED APPLICATIONS

This application claims the benefit under 35 U.S.C. § 119(e) of U.S. Provisional Application No. 62/585,957, filed on Nov. 14, 2017, which is incorporated by reference herein in its entirety.

BACKGROUND OF THE INVENTION

Field of the Invention

The present invention relates to an apparatus and a method for applying plasma-activated liquids and gases to plants and in agricultural settings.

BRIEF SUMMARY OF THE INVENTION

In an embodiment, a method for production of plasma-activated liquids is described. The method includes immersing a first electrode and a second electrode into liquid in a container, and energizing, by a high voltage power supply, the first electrode and the second electrode to form a plasma between the first electrode and the second electrode to thereby generate plasma-activated liquid. The method also includes etching material from at least one of the first electrode and the second electrode into the plasma-activated liquid.

In another embodiment, a method for applying plasma gas to plants is described. The method includes passing a gas through a dielectric cylinder from one end to another end, and energizing, by a high voltage power supply, an inner electrode and an outer electrode to generate the plasma gas from the gas, wherein the inner electrode is disposed inside of the dielectric cylinder and the outer electrode circumscribes an outside of the dielectric cylinder. The method includes delivering the plasma gas to a plant.

In yet another embodiment, a system is described that is configured to apply plasma gas in an agricultural setting. The system includes a dielectric cylinder having a proximal end and a distal end, as well as an inner electrode disposed inside of the dielectric cylinder, and an outer electrode circumscribing an outside of the dielectric cylinder. The system further includes one or more pipes coupled to the dielectric cylinder, the inner electrode and the outer electrode, the one or more pipes configured to source gas to the proximal end of the dielectric cylinder for flow through to the distal end, and wherein the one or more pipes are further configured to support wiring to the inner electrode and the outer electrode. The system also includes a high voltage power supply coupled to the wiring to provide energy to thereby generate the plasma gas from the gas, as well as an outlet coupled to the distal end, the outlet being configured to apply the plasma gas in the agricultural setting.

Further features and advantages, as well as the structure and operation of various embodiments, are described in detail below with reference to the accompanying drawings. It is noted that the specific embodiments described herein are not intended to be limiting. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form a part of the specification, illustrate embodiments of the present disclosure and, together with the description, further serve to explain the principles of the disclosure and to enable a person skilled in the pertinent art to make and use the embodiments.

Figure 1:
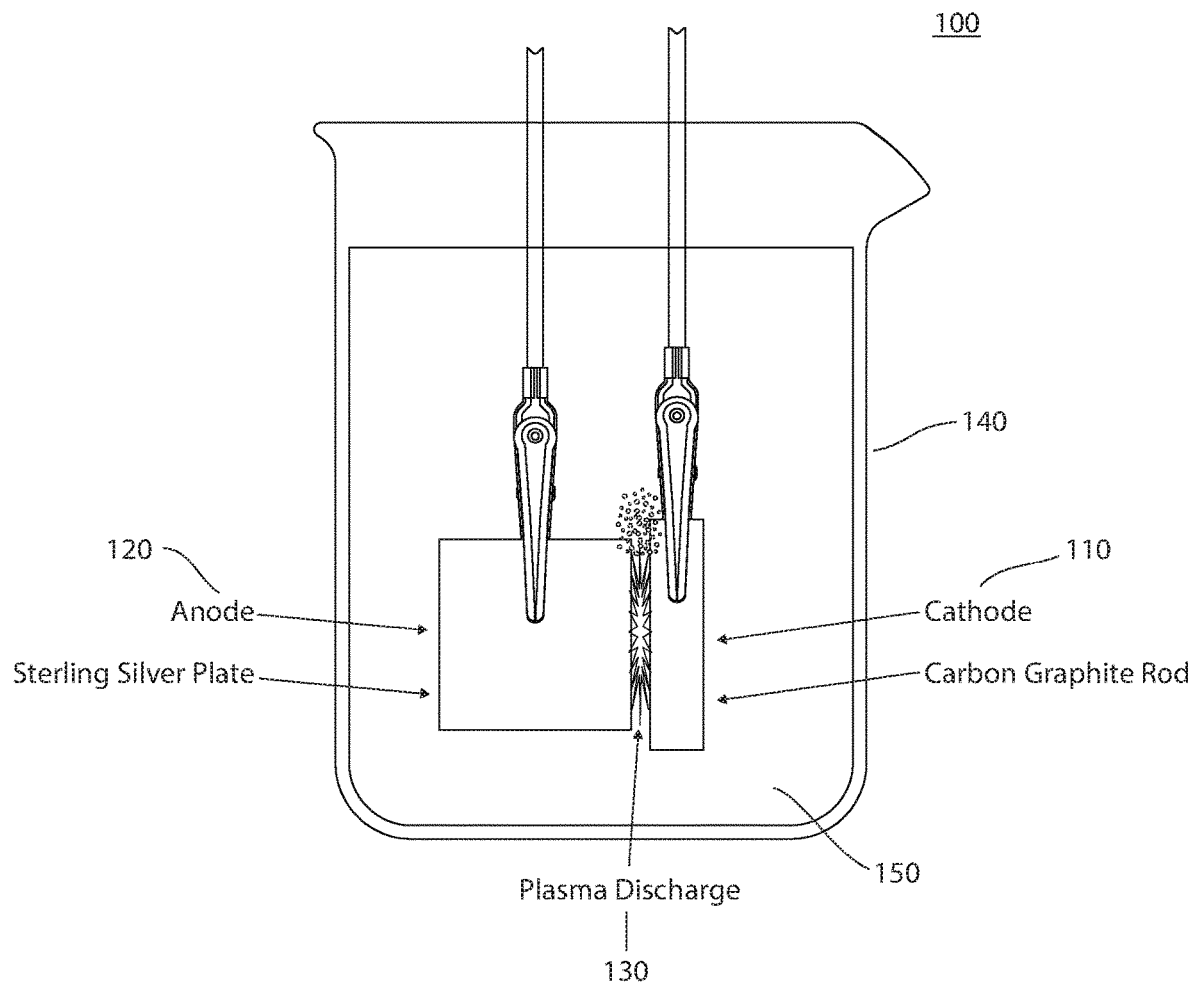
FIG. 1 illustrates an apparatus having an electrically insulative container of water in which a silver plate anode is placed in proximity to a carbon graphite rod, according to an embodiment of the present disclosure.

The present disclosure will be described with reference to the accompanying drawings. In the drawings, like reference numbers indicate identical or functionally similar elements. Additionally, the left most digit(s) of a reference number identifies the drawing in which the reference number first appears.

DETAILED DESCRIPTION OF THE INVENTION

The following Detailed Description refers to accompanying drawings to illustrate exemplary embodiments consistent with the disclosure. References in the Detailed Description to "one exemplary embodiment," "an exemplary embodiment," "an example exemplary embodiment," etc., indicate that the exemplary embodiment described may include a particular feature, structure, or characteristic, but every exemplary embodiment may not necessarily include the particular feature, structure, or characteristic. Moreover, such phrases are not necessarily referring to the same exemplary embodiment. Further, when a particular feature, structure, or characteristic is described in connection with an exemplary embodiment, it is within the knowledge of those skilled in the relevant art(s) to affect such feature, structure, or characteristic in connection with other exemplary embodiments whether or not explicitly described.

The exemplary embodiments described herein are provided for illustrative purposes, and are not limiting. Other exemplary embodiments are possible, and modifications may be made to the exemplary embodiments within the spirit and scope of the disclosure. Therefore, the Detailed Description is not meant to limit the invention. Rather, the scope of the invention is defined only in accordance with the following claims and their equivalents.

The following Detailed Description of the exemplary embodiments will so fully reveal the general nature of the invention that others can, by applying knowledge of those skilled in relevant art(s), readily modify and/or adapt for various applications such exemplary embodiments, without undue experimentation, without departing from the spirit and scope of the disclosure. Therefore, such adaptations and modifications are intended to be within the meaning and plurality of equivalents of the exemplary embodiments based upon the teaching and guidance presented herein. It is to be understood that the phraseology or terminology herein is for the purpose of description and not of limitation, such that the terminology or phraseology of the present specification is to be interpreted by those skilled in relevant art(s) in light of the teachings herein.

Disclosed herein are apparatuses and methods for generating and applying plasma-activated liquids to plants, soil or water reservoirs to alter plant growth (i.e., influence growth rate, reduce time to maturity or harvest), increase plant yield, improve plant health and/or mitigate pathogens.

The following embodiments of generating and applying a plasma-activated liquid are meant to serve as exemplary only and are not intended to limit the scope of the inventive concept. It will be apparent to persons skilled in the relevant art that various changes in form and detail can be made therein without departing from the spirit and scope of the invention. Thus, the breadth and scope of the present invention should not be limited by and of the described exemplary embodiments herein.

A specific example of a system and method of generating a plasma-activated liquid and applying the plasma-activated liquid is described below, followed by other variables that may be incorporated into this system and method. In various embodiments, two electrodes composed of graphite are submerged into a container of water. In one embodiment, the water can be 250 ml distilled water at 95° C., although these values are for illustrative purposes. In various embodiments, the shape of the graphite electrodes can be substantially cylindrical (i.e., rod shaped, but this is not intended to be limiting, as spherical, conical, planar, and other electrode shapes are contemplated) in cross section. In a particular embodiment, the cross section of the electrodes has a diameter of approximately 6 mm and a length of approximately 25 mm. One of the electrodes is electrically coupled to earth ground using a wire. The other electrode is electrically coupled to the output of a high voltage radio frequency (RF) power supply. In one embodiment, the RF power supply is configured to generate approximately 30 kV peak to peak RF voltage, at multiple simultaneous frequencies that are primarily concentrated between 200 and 600 kHz. In this embodiment, the RF power supply is further pulsed on and off at 500 Hz. The distance between the two electrodes is adjusted until a bright electrical arc (plasma discharge) is sustained. In one particular embodiment, the distance between the two electrodes is approximately 1 mm to 4 mm. The distance between the electrodes is periodically adjusted to maintain the arc since material is etched from the electrodes into the liquid. In various embodiments, the electrodes are held in a fixture that allows the distance to be finely controlled by turning a knob and gear assembly.

Various embodiments use predetermined times of arcing. For example, the arcing can be sustained for approximately 5 minutes, 10 minutes, or 30 minutes, or until the desired amount of carbon is suspended in the liquid or until a desired chemistry of water is achieved. A desired chemistry of water (or liquid) may include the water (liquid) reached a desired measured property, such a level of reactive oxygen species (ROS) produced, acidity level, level of free radicals, and the like. In various embodiments, the electrode material (e.g., carbon) is filtered out of the solution. In some embodiments, the filtering of the electrode material is necessary because the solution becomes more conductive as electrode material is etched and suspended in the liquid. At some point, the plasma arc is not generated/sustained because the liquid has become too conductive. In some embodiments, the filtered electrode material may be a useful by-product of the processes described above. This carbon-enriched plasma-activated liquid is then mixed with a standard plant nutrient solution in approximately a 1:10 ratio. The carbon enriched nutrient solution is then applied to growing plants through direct application (e.g., watering when the liquid is water), or is introduced into the reservoir of a hydroponic delivery system. Over the course of 1-4 weeks of periodic carbon-enriched water application (1-2 times per week), the plants grow more vigorously (taller, broader, increased root development) and achieve a significantly higher harvest mass than plants watered with a comparable nutrient solution in a controlled experiment. The following features and descriptions apply more generally to the specific system and method described above:

More generally, other embodiments have a device that has at least two electrodes energized by a high voltage power supply. The electrodes are submerged in a liquid, an electrical gradient is applied between the electrodes that leads to the generation of an electrical arc, whereby the electrical arc leads to removal and deposition of the electrode material into the liquid. In various embodiments, the liquid can be distilled water, tap water, or an ion rich solution such as a nutrient solution for plant growth.

The electrodes in various embodiments are composed of a conductive material, where the conductive material is selected from graphite, tungsten, silver, gold, titanium, copper or similar materials. In various embodiments, the two electrodes may be composed of the same material, and that such material may be selected based on its impact on plant biology. In other embodiments, the two electrodes may be composed of different materials, and that each material may be selected based on a number of factors including impact on plant biology. As noted above, electrode material is deposited in the solution, and is suspended in the solution at micro-sized and nano-sized particles. The removal of the electrode material from the electrodes may be achieved as a result of electrical etching. In certain embodiments, the suspended electrode material(s) may generate chemical reactions or physical interactions, such as absorption with the liquid contents, or between the liquid contents and the electrode material. For example, nutrients may be adsorbed on the surface on the electrode material (e.g., carbon) after the electrode material is produced during the plasma-activated liquid production. Those chemical reactions may be assisted by the application of electrical energy.

Embodiments include a power supply to provide the electrical energy. Various power supplies may be used, including a DC power supply, a pulsed DC power supply (exemplary pulse widths include microsecond, millisecond and nanosecond pulse widths), alternating current (AC) power supply, a pulsed AC power supply, an RF power supply, a pulsed RF power supply, and a power supply that provides microwave energy. Other embodiments of power supplies include an AC power supply that provides multiple harmonic-rich frequencies that are generated simultaneously.

In embodiments, the power supply provides energy to one of the electrodes, while the other electrode may be grounded. Alternatively, the other electrode may be a node for supply of an opposing phase of an alternating current waveform. In various options, the opposing phase may be a substantially equal and opposite potential to that of the first electrode, of a lower amplitude of an opposing alternating current waveform, or a lower amplitude of an in-phase alternating current waveform.

As noted above, embodiments may be used in agriculture, including the application of plasma-activated liquids to plants. In various applications, the plants include vegetables, fruits, medicinal, ornamental, and algae. Plants are grown in a variety of growth media, including: soil, soilless mixes (coconut fiber, perlite, vermiculite), sphagnum moss, rockwool, clay pellets, water absorbing polymers, and other media generally known in the art. Application of the plasma-activated liquids incudes application in the root zone or on the foliage of the plants. Root zone application includes watering using direct watering, drip irrigation, and hydroponic irrigation methods. Foliage applications includes spraying, misting, ultrasonic atomization, electro-spraying and similar approaches.

The plasma-activated liquid application offers various benefits, including the improvement of plant growth, root structure, leaf quality, fruit quality, flower quality, and/or plant yield. Benefits also include improvement of the growth rate of the plant (i.e., a reduced time to maturity or harvest). Other benefits also include the destruction of pathogens, where the pathogens may include fungus, oomycetes, bacterium, and viruses. Specific examples of pathogens may include powdery mildew, fusarium, botrytis, tobacco mosaic virus, and the like.

Certain benefits may be coordinated with certain aspects of certain embodiments. For example, the electrode material introduced to the liquid may be selected to achieve the desired biological effect and in accordance with the particular application method used (i.e., root zone vs. foliage). In a specific example, a graphite material may be selected to improve plant growth and yield when liquid is applied to the root zone. In another example, a silver material may be selected to destroy pathogens when liquid is applied to the root zone or foliage.

Embodiments of plasma-activated liquid generation apparatus include stand-alone systems, as well as integrated applications. A stand-alone system embodiment may be used to produce plasma-activated liquid (e.g., water), which is then "bottled" for future use for plants. An integrated application includes use in an existing agricultural grow facility, where the plasma-activated liquid (e.g., water) is directly pumped or directly flows into the grow facility and administered to the plants. In any of these embodiments, the plasma-activated liquid may be first diluted into water or nutrient solutions. Another integrated application includes use in an agricultural farm or field, where the plasma-activated liquid (e.g., water) is directly pumped or directly flows into the farm or field and administered to the plants. In any of these embodiments, the plasma-activated liquid may be first diluted into water or nutrient solutions.

Other embodiments include methods of generating a plasma-activated liquid. In an exemplary embodiment, the method includes immersing two or more electrodes in a solution, applying a difference in high voltage potential to the two or more electrodes, generating an electrical arc between the two or more electrodes, removing electrode material from one or more electrodes into the liquid, and applying the liquid to a plant. In one embodiment, applying the liquid to a plant includes applying the liquid to the root zone of the plant. In another embodiment, applying the liquid to a plant includes applying the liquid to the foliage of the plant. In various alternative embodiments, the liquid is mixed with other liquids prior to application to the plant. In embodiments, the other liquids include water, and a nutrient solution suitable to sustain plan growth. In a further embodiment, the method includes plasma-activating a liquid(s) to change the properties of the liquid(s) to be nutritionally superior for the purpose of improving plant growth cycle, health, immunity and/or yield.

In a further embodiment of generating a plasma for agricultural use, a plasma discharge is generated in a gaseous environment and the gas plasma is directed towards a plant to reduce the growth of plant pathogens. In one exemplary embodiment, an inner electrode is placed inside of a cylinder made of a dielectric material. A ring-shaped outer electrode circumscribes the outside of the dielectric cylinder, and the ring-shaped electrode is connected to earth ground. In an exemplary embodiment, the ring-shaped electrode is approximately 55 m in diameter. The inner electrode consists of a dielectric coated conductive material and is connected to a high voltage power supply. By way of example, the dielectric material may be glass and the electrode may be created by a conductive paint applied to the inner walls of a sealed-end glass cylinder. In a particular example, the inner electrode is approximately 15 mm in outside diameter, and there is a space of approximately 20 mm between the outside diameter of the inner electrode and inside diameter of the dielectric cylinder wall. A gas is made to flow through the dielectric cylinder from one end to the other. The inner electrode is energized with a high voltage RF electrical energy source thereby generating an electrical discharge between the outside diameter of the inner electrode dielectric and the inside diameter of the outer electrode dielectric. In a particular example, the high voltage RF electrical energy source is approximately 35 kV peak to peak. This electrical discharge ionizes the gas passing through the cylinder generating a plasma. By way of example, the gas may be air. A hose or other means of delivery may be attached to the distal end of the plasma generating cylinder. An air pump or fan may be used to flow air through the core of the cylinder and through the discharge zone where ionization takes place. The flow of air pushes the plasma out of the distal end of the device. The reactive chemical species, such as reactive oxygen species and reactive nitrogen species, exit the distal end of the plasma generating cylinder. These reactive species, along with other charged species from the plasma discharge, are sprayed onto a plant surface. The plasma discharge interacts with microbes on the surface, or subsurface, of the plant rendering them nonviable. This system has demonstrated effectiveness on a range of fungal and bacterial strains that commonly infect plants and have a negative impact on the agriculture industry including; powdery mildew, botrytis, and *E. coli*. It should be appreciated that the destruction of these pathogens would be valuable at all stages of plant production including, seeds, seedlings, growing plants, and the sanitation of agricultural products after harvest.

The above system embodiments may be easily configured in a hand-held device that can be pointed and directed, by a human or automated actuator, at different target areas of a plant. The power supply may be backpack mounted or cart mounted to allow for a lightweight and maneuverable hand-held plasma applicator. In an alternate embodiment, a centrally located power supply may be used to power smaller plasma generators that are dispersed around an agricultural facility in arrays, such that activating the system will deliver plasma-activated gas to a large area of growing plants simultaneously. This could be used to "blanket" and area in plasma-activated gas and sanitize large areas.

As would be appreciated by one skilled in the art, the apparatus described above may be modified in several ways yet still achieve the intended purpose. For example, the dielectric materials may be glass, ceramic, PTFE, Delrin, or other well-known plastic dielectric materials. The electrode materials may be copper, tungsten, carbon, or conductive paints/coatings. The diameters of the inner and outer cylinders could be altered, as long as the distance between the two remained sufficient to sustain a plasma discharge at the applied voltage. The waveform of applied voltage could be modified, e.g. DC, pulsed DC, AC, RF, pulsed RF, and microwave of different frequencies. The earth ground electrode could be connected to an alternating phase of the power supply. Multiple ring-shaped electrodes could be introduced to the outer cylinder in order to control the pattern of plasma generated. Of the multiple ring-shaped electrodes, only certain electrodes may be connected to earth ground, and/or to an alternating phase of the power supply, in order to further control the plasma generation. The flow rate of gas could be altered to achieve the desired concentration of reactive species based on dwell time in the plasma chamber. The gas composition could be modified to include noble gases such as helium or argon, could be enriched with oxygen or nitrogen, or combinations thereof.

Embodiments include a method of treating plant pathogens using a plasma reactor chamber that contains at least two electrodes, whereby energy is passed between the at least two electrodes, a gas is passed through the plasma reactor chamber, the outflow port is directed at a plant which is colonized by a pathogen, and the pathogen is reduced in number or viability by the plasma gas outflow.

Embodiments include a method of generating a plasma-activated liquid for application to a plant whereby an electrical arc is generated in a containment chamber as described above, a gas is passed through the containment chamber, the gas is bubbled through a liquid, the liquid is then applied to a plant. A porous stone may be used to increase the surface area of the gas bubbling through the liquid. The liquid may consist of pure water or may contain other chemicals or dissolved salts. In one embodiment, the liquid contains potassium bicarbonate and the plasma-activated liquid is used for foliar application to growing plants. In another embodiment, the liquid contains hydrogen peroxide (e.g., 1% hydrogen peroxide) and after plasma bubbling is used for foliar application. In a third embodiment, the liquid contains copper salts and is applied to the root zone for the treatment of fungus.

FIG. 1 illustrates an apparatus having an electrically insulative container of water in which a silver plate anode is placed in proximity to a carbon graphite rod, according to an embodiment of the present disclosure. In FIG. 1, a container 140 contains a liquid 150. Immersed in liquid 150 are two electrodes, cathode 110 and anode 120. In an embodiment, cathode 110 is made of graphite, and anode 120 is made of silver. When cathode 110 and anode 120 are energized, a plasma discharge 130 is formed.

Figure 2:
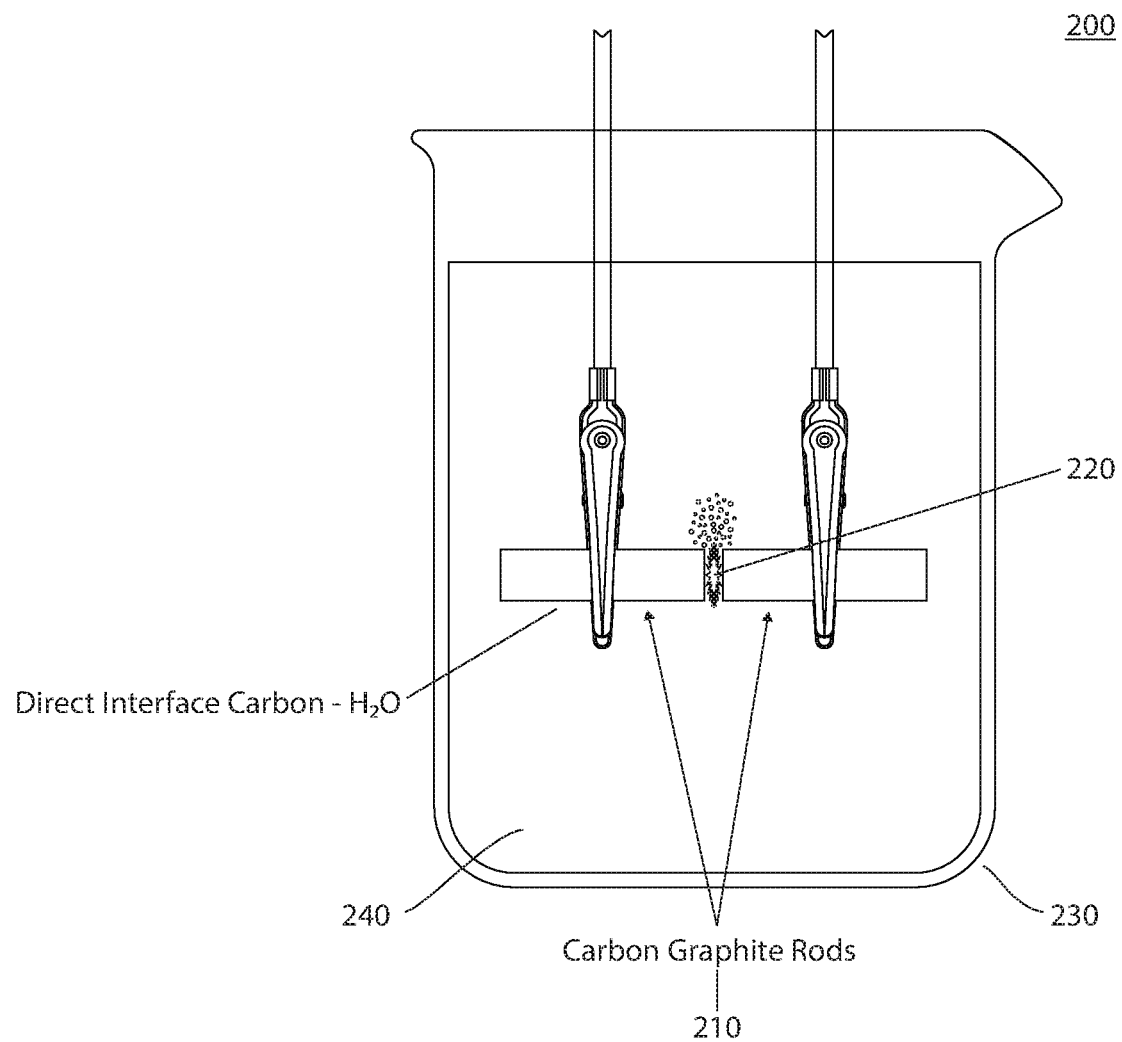
FIG. 2 illustrates an apparatus having an electrically insulative container of water in which two carbon graphite rods are placed, according to an embodiment of the present disclosure.

FIG. 2 illustrates is an apparatus having an electrically insulative container of water in which two carbon graphite rods are placed, according to an embodiment of the present disclosure. Container 230 contains water 240 (or another liquid). Immersed in water 240 are two electrodes 210, which in an embodiment are carbon graphite rods. When electrodes 210 are energized, a plasma 220 is formed.

Figure 3:
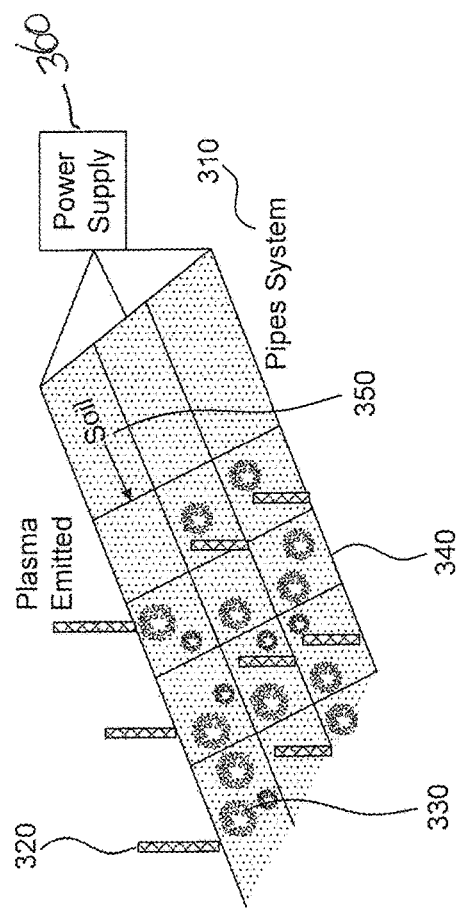
FIG. 3 illustrates a plasma discharge grid used to generate plasma in a gaseous environment, where the gas plasma is directed towards a plant to reduce the growth of plant pathogens, according to an embodiment of the present disclosure.

FIG. 3 illustrates a plasma discharge grid used to generate plasma in a gaseous environment, where the gas plasma is directed towards a plant to reduce the growth of plant pathogens, according to an embodiment of the present disclosure. In this embodiment, a pipe system 310 is used to deliver electrical energy and gas to plasma gas distribution points 320 for application to plants 330. Plants 330 are being grown in soil 350. Pipe system 310 receives the electrical energy from power supply 360. Pipe system 310 receives gas from a gas supply (not shown).

Figure 4:
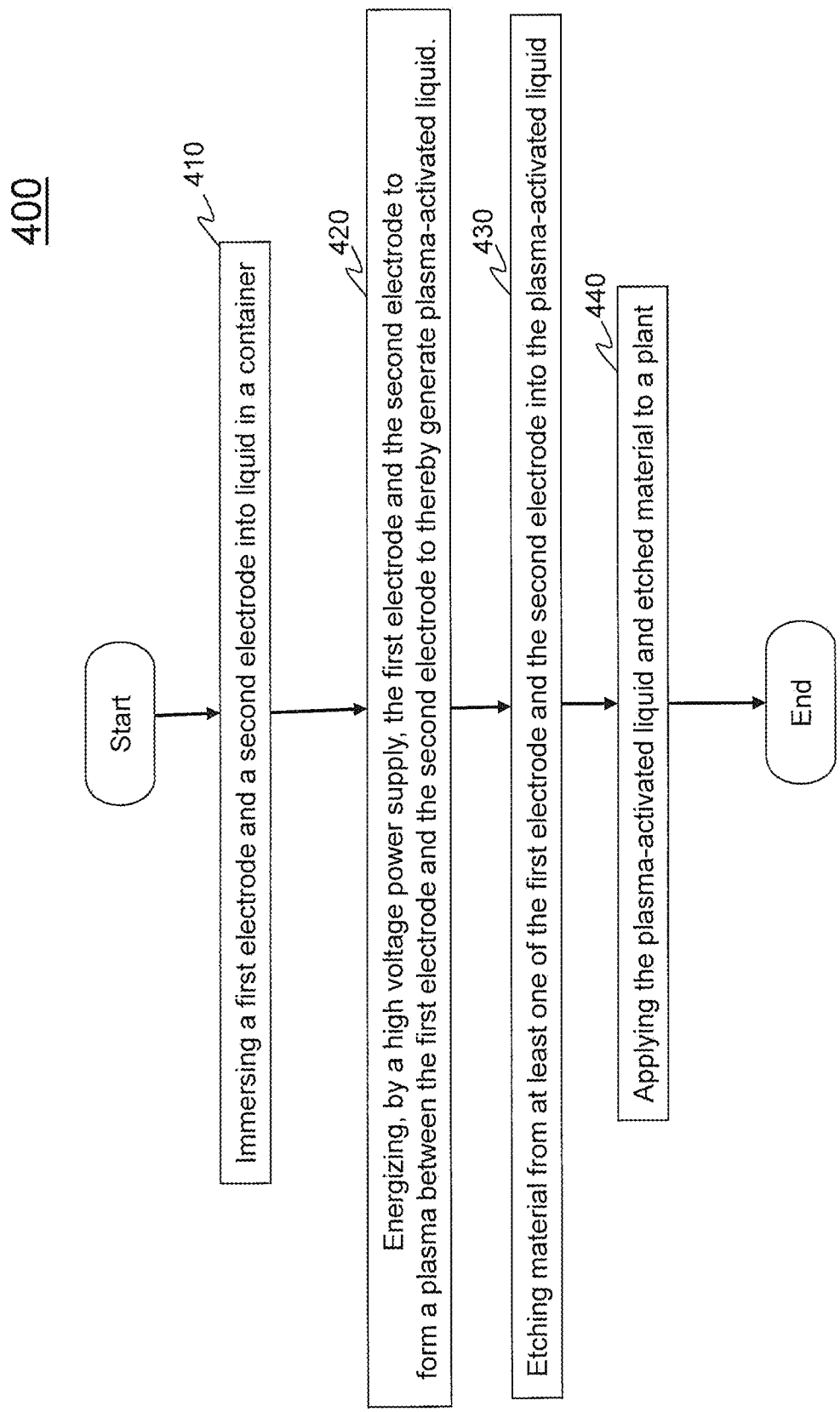
FIG. 4 illustrates a method for applying a plasma-activated liquid to a plant, according to an embodiment of the present disclosure.

FIG. 4 illustrates a method for applying a plasma-activated liquid to a plant, according to an embodiment of the present disclosure. In step 410, a first electrode and a second electrode is immersed into liquid in a container. In step 420, the first electrode and the second electrode are energized by a high voltage power supply to form a plasma between the first electrode and the second electrode to thereby generate plasma-activated liquid. In step 430, material is etched from at least one of the first electrode and the second electrode into the plasma-activated liquid. In step 440, the plasma-activated liquid and etched material is applied to a plant.

It will be apparent to those skilled in the relevant art(s) that various changes in form and detail can be made therein without departing from the spirit and scope of the disclosure. Thus, the disclosure should not be limited by any of the above-described exemplary embodiments, but should be defined only in accordance with the following claims and their equivalents.

What is claimed is:

1. A system configured to apply plasma gas in an agricultural setting, the system comprising:
    a dielectric cylinder having a proximal end and a distal end;
    an inner electrode disposed inside of the dielectric cylinder;
    an outer electrode circumscribing an outside of the dielectric cylinder;
    one or more pipes coupled to the dielectric cylinder, the inner electrode and the outer electrode, the one or more pipes configured to source gas to the proximal end of the dielectric cylinder for flow through to the distal end, and wherein the one or more pipes are further configured to support wiring to the inner electrode and the outer electrode;
    a high voltage power supply coupled to the wiring to provide energy to thereby generate the plasma gas from the gas; and
    an outlet coupled to the distal end, the outlet being configured to apply the plasma gas in the agricultural setting.

2. The system of claim 1, wherein the gas is air.

3. The system of claim 1, wherein the outlet is further configured to apply the plasma gas to a plant in the agricultural setting.

4. The system of claim 1, wherein the high voltage power supply includes a DC power supply, an AC power supply, a pulsed DC power supply, a pulsed AC power supply, a harmonic RF power supply, or a RF power supply operating at microwave frequencies.

5. The system of claim 1, wherein the one or more pipes are configured in an array.

6. The system of claim 1, wherein the inner electrode comprises a dielectric coated conductive material.

7. The system of claim 6, wherein the inner electrode comprises a glass cylinder having sealed ends, wherein the glass cylinder comprises an inner wall that is coated with a conductive paint.

8. The system of claim 1, wherein the high voltage power supply comprises a high voltage radiofrequency electrical energy source.

9. The system of claim 1, wherein the outlet comprises a hose.

10. The system of claim 1, further comprising an air pump or fan configured to flow air through the dielectric cylinder and push plasma gas out of the distal end of the dielectric cylinder.

11. The system of claim 1, wherein the dielectric cylinder, inner electrode, outer electrode, and one or more pipes are provided as components of a hand-held device.

12. The system of claim 11, wherein the high-voltage power supply is configured to be selectively mounted to a backpack or cart.

13. A method for applying plasma gas in an agricultural setting, the method comprising:
using one or more pipes to source gas to a proximal end of a dielectric cylinder, wherein the one or more pipes are coupled to the dielectric cylinder, wherein the gas flows through the dielectric cylinder from the proximal end of the dielectric cylinder to a distal end of the dielectric cylinder;
energizing, by a high voltage power supply, an inner electrode and an outer electrode to generate the plasma gas from the gas, wherein the one or more pipes are coupled to the inner electrode and the outer electrode, wherein the one or more pipes support wiring to the inner electrode and the outer electrode, wherein the inner electrode is disposed inside of the dielectric cylinder, wherein the outer electrode circumscribes an outside of the dielectric cylinder, and wherein the high voltage power supply is coupled to the wiring to provide energy to thereby generate the plasma gas from the gas; and
using an outlet coupled to the distal end of the dielectric cylinder to apply the plasma gas in the agricultural setting.

14. The method of claim 13, wherein the gas is air.

15. The method of claim 13, wherein the high voltage power supply is a high voltage RF electrical energy source that generates an electrical discharge between an outside diameter of the inner electrode and an inside diameter of the outer electrode, wherein the electrical discharge ionizes the gas passing through the dielectric cylinder, thereby generating the plasma gas.

16. The method of claim 13, wherein the plasma gas is applied onto a plant surface.

17. The method of claim 16, wherein the plasma gas is applied onto a root zone of a plant.

18. The method of claim 16, wherein the plasma gas is applied onto foliage of a plant.

19. The method of claim 16, wherein reactive species within the plasma gas interact with one or more microbes on the plant surface to render the one or more microbes nonviable.

20. The method of claim 13, wherein the one or more pipes are configured in an array within an agricultural facility.

* * * * *